(12) United States Patent
Crosby

(10) Patent No.: US 6,217,744 B1
(45) Date of Patent: Apr. 17, 2001

(54) DEVICES FOR TESTING FLUID

(76) Inventor: Peter Crosby, 5550 169th Pl., SE., Bellevue, WA (US) 98006

( * ) Notice: Subject to any disclaimer, the term of this patent is extended or adjusted under 35 U.S.C. 154(b) by 0 days.

(21) Appl. No.: 09/216,389

(22) Filed: Dec. 18, 1998

(51) Int. Cl.⁷ .................................................. G01N 27/26
(52) U.S. Cl. .......................... 205/775; 429/118; 204/400; 422/52; 422/55; 422/56; 422/68.1; 422/82.01; 422/50
(58) Field of Search ..................................... 429/118, 149, 429/162, 128; 204/400, 430, 403, 416, DIG. 3, DIG. 4; 205/775, 789, 792; 324/425; 422/52, 55, 56, 57, 61, 68.1, 82.01, 82.05, 82.06, 82.02, 82.03, 50

(56) References Cited

U.S. PATENT DOCUMENTS

| | | | |
|---|---|---|---|
| 4,185,143 | * 1/1980 | Birt et al. | 429/119 |
| 4,787,398 | 11/1988 | Garcia et al. | 128/770 |
| 4,805,624 | * 2/1989 | Yao et al. | 600/345 |
| 4,822,698 | * 4/1989 | Jackovitz et al. | 429/27 |
| 5,279,294 | 1/1994 | Anderson et al. | 128/633 |
| 5,371,687 | 12/1994 | Holmes, II et al. | 364/514 |
| 5,491,097 | 2/1996 | Ribi et al. | 436/518 |
| 5,653,939 | 8/1997 | Hollis et al. | 422/50 |
| 5,660,993 | 8/1997 | Cathey et al. | 435/7.9 |
| 5,796,345 | * 8/1998 | Leventis et al. | 340/604 |
| 5,837,546 | * 11/1998 | Allen et al. | 436/169 |
| 5,909,114 | * 6/1999 | Uchiyama et al. | 324/94 |

* cited by examiner

Primary Examiner—T. Tung
Assistant Examiner—Alex Noguerola
(74) Attorney, Agent, or Firm—Gottlieb, Rackman & Reisman, P.C.

(57) ABSTRACT

An improvement is described to disposable devices for performing chemical or biological tests on a sample of fluid, and the method by which such devices perform tests. The power for the device comes from an electrochemical battery, where a portion of the fluid sample itself provides the electrolyte for the battery. Furthermore, the time of diffusion of the fluid into the battery provides the timing signal for activation of the system. Communication between the improved device and an information system is provided by a transponder system built into the device which requires no direct electrical connection. Rather, the device is placed in proximity with a reader which can interrogate the device, obtain the results of the test and if necessary provide power for the device to perform the test, and/or communicate the information. The improvements and methods are particularly applicable to devices for performing in vitro diagnostic tests on a sample of body fluid.

32 Claims, 2 Drawing Sheets

DEVICES FOR TESTING FLUID

A. FIELD OF THE INVENTION

This invention pertains to disposable devices for performing chemical or biological tests on a fluid sample, and more particularly devices for performing in vitro diagnostic tests on a sample of body fluid.

B. BACKGROUND OF THE INVENTION

There are many applications where a fluid sample is to be tested for certain physical characteristics (such as electrical conductivity), or the presence of certain chemical or biological species (analytes). Such testing methods may involve a chemical reaction which can take some time to complete before the result is available to be read. The result can be read with a variety of methods such as electrical conductivity, optical density at a certain wavelength of light spectrophotometric), detection of presence of a color, fluorescence, luminescence, or a biosensor. Such applications include pollution monitoring and testing of salinity of drinking water. Another important area of application is the testing of a sample of biological fluid.

Diagnosis of many clinical conditions requires the detection of small quantities of specific chemicals in the person's body. In-vitro diagnostic devices (IVDs) are used to perform tests on samples such as urine, blood, saliva, or other body fluids. Most in vitro diagnostic tests are performed in the central laboratory of a hospital, and often by large expensive machines designed for batch processing of large numbers of samples which may require a panel of a number of tests. The results of the analysis are generally made available via the Laboratory Information System (LIS) to the hospital computer system for access by physicians at many sites throughout the hospital or clinic.

There are some clinical conditions where the central laboratory style of IVD testing often can not satisfy the need, either because of convenience or requirement for immediate results. In response to this clinical and market need, several companies have developed devices for portable, or near patient or so called Point of Care (POC) in vitro diagnostic tests. The instrument size and complexity depends on the application, from bench top to small enough to be worn in a shirt pocket.

For example, there are several companies today which provide small, battery powered, portable hand held instruments for testing of glucose in blood or urine. The availability of these devices has been a boon to diabetics who need to frequently test for blood glucose levels. These devices often consist of a small battery powered console, and a disposable test strip or cartridge. The fluid sample is placed into an aperture or onto a marked place on the test strip, and then the strip is placed into a reader, which reads some parameter of the chemicals to provide a quantitative (i.e.: numerical) or qualitative result. See, for example, the device described by Anderson et al in U.S. Pat. No. 5,279, 294 Medical Diagnostic System, which uses a disposable lancet and reagent unit with a small battery powered portable instrument for measuring blood glucose. A similar device is described by Garcia et al in U.S. Pat. No. 4,787, 398, Glucose Medical Monitoring System.

Another application where the central laboratory style of testing has limitations is in detection of acute myocardial infarct (AMI or heart attack) in patients who present to a hospital emergency room with chest pain. The current state of the art is to immediately test for a panel of cardiac related biochemical markers, which individually and in combination, can reveal the presence of an AMI. The most commonly used cardiac markers are Myoglobin, creatine kinase in its muscle/brain isoform (CK-MB), and Troponin.

The cardiac panel can be performed on serum or plasma (i.e.: blood from which the red blood cells have been removed), or on whole blood. There is an advantage in performing the tests on whole blood because it avoids the step of centrifuging blood to generate serum or plasma, and therefore may save vital minutes to a definitive diagnosis and allow earlier therapy delivery.

Most POC IVDs employ a variation on the same theme. An instrument is used to "read" the results from a disposable cartridge into which a small volume of sample has been placed. Larger instruments frequently can be connected to the LIS, whereas smaller ones often lack this feature.

Technologies to perform the reading include traditional chemistry such as spectrophotometry, biosensors (where the electrical properties of a sensor are affected by the presence of the analyte—see, for example, Ribi et al U.S. Pat. No. 5,491,097, Analyte Detection with Multilayered Bioelectronic Conductivity Sensors), immunofluorescence and immunoluminescence, to name a few. The techniques for managing fluid flow between the fluid sample and the reagents are well explored in a disposable device—see, for example, the work of Cathey et al as described in U.S. Pat. No. 5,660,993, Disposable Device in Diagnostic Assays.

In many of these systems, the chemistry system reacts with the analyte in the fluid sample, and an optically active marker chemical is excited with a laser at a particular wavelength, and then fluoresces at a different wavelength which is detected by a photodetector such as a photodiode or photomultiplier. Such instruments are made, for example, by Biosite Inc. (San Diego), or First Medical (Mountain View, Calif.). Another technology is surface plasmon resonance used in devices made by Quantech, Inc. (Minneapolis, Minn.).

The pressure for continuing miniaturization and reduction in cost is relentless. Electronic microcircuit fabrication technologies have been pressed into service to make sensor systems for multiple analytes, on a single chip, such as described by Hollis et al in U.S. Pat. No. 5,653,939, Optical and Electrical Methods and Apparatus for Molecule Detection. In recent years, electronic technology has progressed to the point where it has become feasible to manufacture at reasonable cost a complete disposable testing device which contains the chemicals necessary to do the test, as well as the optical and electronic components to read and display the result, and communicate the information to a hospital information system. Such a device is described in U.S. Pat. No. 5,279,294 Medical Diagnostic System by Anderson et al.

Although this device (manufactured and marketed by Metrika Inc, Mountain View, Calif.) and others like it represent a potential tremendous advance, it suffers from some serious limitations. Firstly, the power for the device is provided by small batteries similar to those used in a camera or a watch. These batteries add cost, weight, and reliability problems, as well as presenting a disposable hazard because of the toxic chemicals such as mercury and cadmium often used in the battery.

Furthermore, communication with the hospital information system or laboratory information system (LIS) is done by an electrical connector on the side of the printed circuit board (PCB) inside the device which mates with a connector on a reader or console which is connected to the LIS. A direct electrical connection requires an aperture to be made into the side of the device, complicating the internal design and adding size, weight and cost (the connector must be gold plated to facilitate reliable connection). Also, a direct electrical connection requires precise registration with the reader, which can be difficult and is fraught with reliability issues. Finally, in a laboratory environment with the presence of various types of fluids and chemicals, the connector on the reader or console could be subject to corrosion and degradation, again leading to poor reliability. Despite these limitations, direct electrical connection is the state of the art and is used in many instruments such as the one described by Holmes and Anderson in U.S. Pat. No. 5,371,687 Glucose Test Data Acquisition and Management System.

The present invention overcomes these limitations, and thereby improve the concept of a disposable self powered in vitro diagnostic device. The methods described are not limited to devices for performing in vitro diagnostic tests, and can be used for any device which operates with a fluid sample, for example, a self powered device for monitoring water pollution.

C. OBJECTIVES AND SUMMARY OF THE INVENTION

A self powered device for performing diagnostic tests on a small sample of fluid is described. The electrical power for the device comes from an electrochemical cell, where a portion of the fluid sample itself provides the electrolyte for the cell, either providing all the ionic species required in the electrolyte, or by dissolving dried salts available in the fluid path. Furthermore, the time of diffusion of the fluid into the cell provides the timing signal for activation of the system.

Communication with the improved device is provided by a transponder system built into the device which requires no direct electrical connection. Rather, the device is placed in proximity with a reader which can interrogate the device and obtain the results of the test.

D. BRIEF DESCRIPTION OF THE DRAWINGS

E. DETAILED DESCRIPTION OF THE PREFERRED EMBODIMENT

The preferred embodiment of the present invention is described as pertaining to a self powered device for performing in vitro diagnostic tests on a sample of body fluid for clinical application. However, the invention is not limited to devices for performing analysis on a sample of body fluid, but to any device which is required to perform analysis on a sample of fluid.

The first improvement described in the present invention is a system for providing electrical power for an in vitro diagnostic device operating on body fluids which contain a significant amount of water (blood, urine, saliva, semen, cerebro-spinal fluid, amniotic fluid, etc). In this invention, power is provided by an electrochemical battery which provides both power and timing signals.

The chemical basis for such a cell can be found in any standard college chemistry text book, and is often illustrated as two dissimilar metal rods (e.g.: copper and zinc) plunged into a lemon with a voltmeter indicating the availability of electrical power. The acids in the lemon provide the electrolyte, and the dissimilar metals provide electrical power, as is described by the familiar Nernst Equation.

A simple experiment illustrates the concept. A demonstration cell is constructed of two electrodes consisting of a piece of copper sheet approximately 1 cm by 2 cm, and a piece of galvanized steel flashing (galvanizing is plating with zinc) slightly larger than the copper electrode, separated by a layer of two sheets of normal blotting paper commonly used for drying ink, with approximately 5 mm protruding from one end. Wires are soldered to the two metal electrodes, and these are connected to a digital voltmeter. The assembly can be held together with rubber bands. The blotting paper is dipped into a sample of urine and, after approximately 1 minute, the blotting paper becomes saturated along its whole length. The open circuit voltage is measured to be approximately 0.67 V (copper is positive with respect to zinc), and the short circuit current is measured to be approximately 0.75 mA, yielding an internal cell impedance of approximately 890 ohms. This cell is able to deliver the short circuit current continuously for over ten minutes. Thus, the cell is able to deliver continuous power of approximately 0.2 mW for over ten minutes, which is adequate for modern day electronic circuits. Refinements in the cell design such as surface preparations to increase the effective surface area and selection of different metals to yield a higher open circuit cell voltage will yield better performance without altering the fundamental concept. Larger surface areas could be achieved by using thin metal foils for the electrodes separated by the porous membrane, folded or rolled to occupy a small volume but large electrode surface area.

Figure 1A:
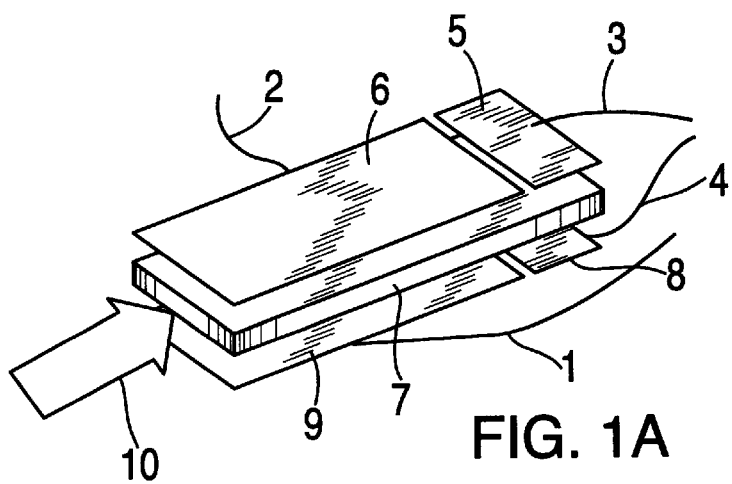
FIG. 1A is an illustration of a battery assembly with four electrodes and a porous separator membrane.

A diagram of the electrochemical battery which powers the fluid testing device is shown in FIG. 1A. The system consists of two electrochemical cells made from plates of dissimilar metals separated by a porous membrane. The two cells in the present invention are referred to as the power cell and the wake up cell. Fluid from the introduced sample flows by capillary action from one end along the porous membrane, thus closing the circuit and allowing current to flow. In many applications, the electrolytic components of the body fluid (eg: $Na^+$, $K^+$, $Cl^-$, $HCO_3^-$) will be sufficient to activate the cell and provide enough power for the electronics to perform the analysis. However, there are others where the sample may have insufficient electrolytes, and in this case the cell is manufactured with dried salts deposited on either or both of the electrodes or embedded in the membrane, which dissolve in the introduced fluid, thus completing the basic electrochemical cell.

The power cell consists of a porous membrane (7) which separates the plates of dissimilar metals (6) and (9). The porous membrane is continuous with the metal plates (5) and (8) which form the wake up cell. The two metal plates could be zinc and copper, or any appropriate metal pair. Fluid enters at one end from the sample reservoir, shown diagrammatically by the arrow (10). As the porous membrane becomes saturated with fluid containing electrolytes, it completes a standard electrochemical cell. In an alternative form the fluid dissolves the crystalline salts embedded in or deposited on the membrane, thus completing the cell. The salts could be zinc chloride and copper chloride. The porous membrane could be made from a variety of materials including paper, cotton, or a woven polymer. Since capillary flow results in the power cell becoming active before the wake up cell, as soon as the wake up cell is active, then sufficient energy will be available to power the electronics. Furthermore, if a certain time is required for the chemical reactions to be completed before the results are available to be read, the battery can be designed such that the time of diffusion of the fluid before the wake up cell is active can be used as the timing signal for the whole system.

Wires (1) and (2) take electrical current from the cell to power the electronics in the disposable device. Separate wires (3) and (4) are used to provide a signal which indicates when the cell is operational, and to "wake up" the microprocessor in the device. The amount of power required to wake up the microprocessor is miniscule, so the area of the wake up cell plates can be small, even as small as a thin wire. The crucial fact is that the wake up cell is only active after the power cell has been activated sufficiently to power the electronics.

The wake up cell delivers an electrical signal (a voltage), but also exhibits lower electrical impedance when the fluid has permeated to this end of the assembly. Therefore, the wake up circuit of the system could be designed to either detect the available voltage from the cell, or the lower electrical impedance across the electrodes. If the detection of wake up is by means of lower impedance, then the cell is not required to deliver energy, and the metal plates or wires could be made of the same material, which could simplify construction.

Figure 1B:
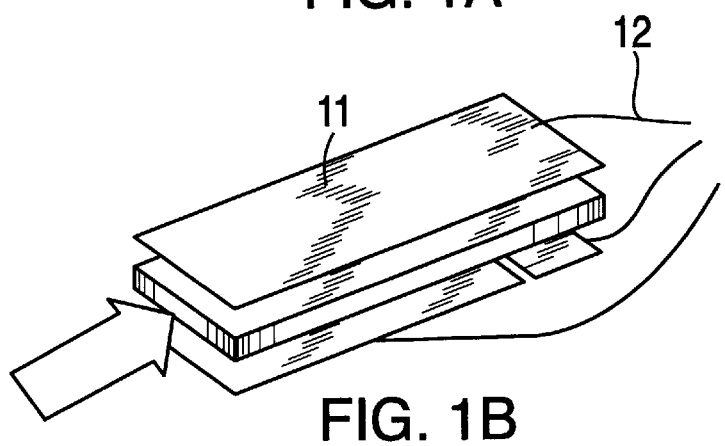
FIG. 1B is an illustration of an alternative embodiment of a battery where the two cells have one electrode in common.

FIG. 1A shows two cells with separate electrode pairs and a common porous separator membrane, but it is possible that one electrode is continuous with both cells as shown in FIG. 1B. In this case, the upper electrode is a single piece of metal (11) with a single lead wire, while the other electrode pair remains separate. This approach could simplify construction and reduce costs.

Figure 2:
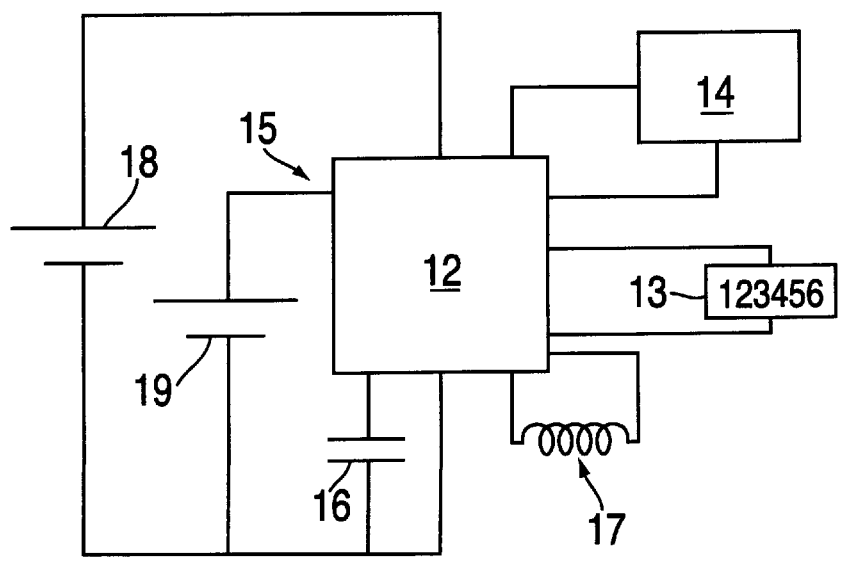
FIG. 2 is a block diagram of the electronics system.

A block diagram of a "generic" self powered in vitro diagnostic device is illustrated in FIG. 2. An electronics module (12), preferably a single silicon chip, consisting of a microprocessor and associated electronics, performs most of the functions. Any one or combination of a variety of well known sensors could be used, shown diagrammatically as a block diagram (14). These could be a diode laser and a photodetector for a system which uses immunofluorescence, or a photodetector for a system which uses immonuluminescence, or an electrical detector such as a potentiometer for a device which uses an electrically active biosensor, or a resistance measuring circuit to determine conductivity.

The electronics subsystem is connected to a display for the results, such as a liquid crystal alpha-numeric display shown as (13). The power cell (18) is connected to the electronics module, as is the wake up cell (18). The wake up cell delivers a signal through the wake up line (15) to the electronics module to indicate when fluid has been entered into the system, and sufficient power is available from the power cell.

The power cell is capable of delivering low level current at typically low voltage. An on-board power regulator in the electronics module is used to double or triple the voltage and provide regulation, and also charges a storage capacitor (16) so that intermittently high power can be delivered for example to the diode laser of a sensor module (14). A coil (17) is connected to the microprocessor for the purposes of data communication as will be explained below.

Figure 3:
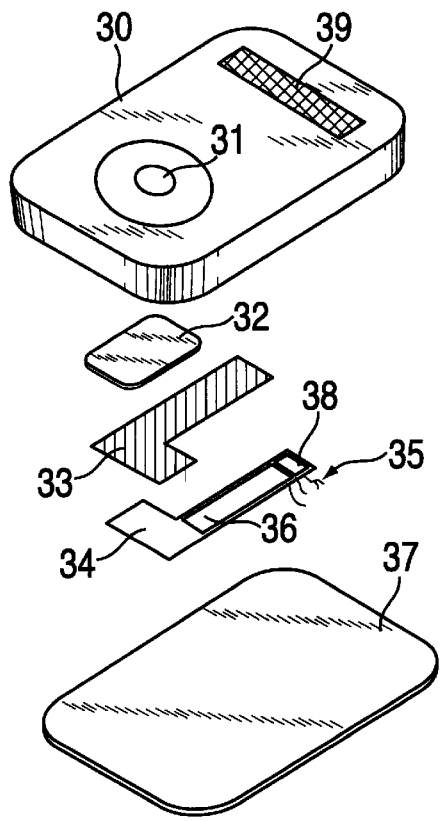
FIG. 3 is an exploded view of the complete self powered measurement device.

An exploded view of the pertinent parts of the assembly of a typical disposable device is shown in FIG. 3. A top cover (30) has a depression or well to accept a fluid sample. A hole in the depression (31) allows fluid to enter the device. The top cover in this example also is the carrier for the electronics and optical components (not shown), and the LCD display (39).

When fluid is placed into the aperture it first contacts a filter (32). The purpose of the filter is to remove particles and cells from the fluid sample, which might be blood. The filtered fluid first contacts a porous membrane (33) which contains the reagents for conducting the chemical analysis. The fluid is drawn along this membrane by capillary action and activates the chemicals which, in this example, are read by the optoelectronic components in the cover (30). Many methods for performing this analysis are described in the prior art and are not the subject of this invention.

Additional fluid contacts the porous membrane (34) which is the separator for the electrochemical cell providing power and timing information for the electronics module. One electrode for the power cell is shown as (36), and one electrode for the wake up cell is shown as (38). Wires for taking the power and timing signals are illustrated diagramatically as (35).

The electrochemical battery in the illustration is shown as separate from the electronics assembly. However, the electronics assembly could be constructed from flexible printed circuit elements, where the printed conductors could comprise the metal plates of the cell. Printed conductors are generally copper, which is an ideal material for one of the electrodes, and the copper could be plated with zinc, nickel, or silver to form the other electrode. With this construction technique, the electronics, power cell, and wake up cell with separator membrane, could be constructed as a single module, thus simplifying manufacturing and reducing costs.

In operation, the fluid is applied to the well, which is then filtered and diffuses into both the chemistry analysis strip and the power cell. The design of the chemistry strip and the electrochemical cells is such that a wake up signal from the wake up cell is available when the chemical reactions are complete and can be read, and sufficient power is available to power the electronics module.

The system is designed to be most power efficient. The time between application of the sample and the availability of the wake up signal is such that the wake up signal is delivered at a time when the reaction between the analyte and the analysis chemical system is complete, and the result is ready to be read. In this way, the system is unpowered until necessary. Furthermore, the high power elements of the system are used briefly. For example, if the sensor system consists of a diode laser and a photodetector, the laser is only turned on long enough to excite the fluorescent markers and to read the signal from the photodetector. The intermittent high power requirements for a laser diode are obtained from the capacitor (16) which is used to store energy from the cell.

In use, the disposable device is packaged in a sealed pouch which may also contain a desiccant material such as silica gel to prevent inadvertent early activation of the system by exposure to fluid.

It is one of the objects of the present invention to provide communication between the disposable analysis device and an information gathering and storage system such as a hospital information system. While it would be possible to directly electrically connect the device to a reader (i.e.: with an electrical connector), there are disadvantages of this approach including cost, potential contamination of the connector, need for precise placement in the connector, and power requirements for communication. The present invention uses a different system of communication based on telemetry.

Figure 4:
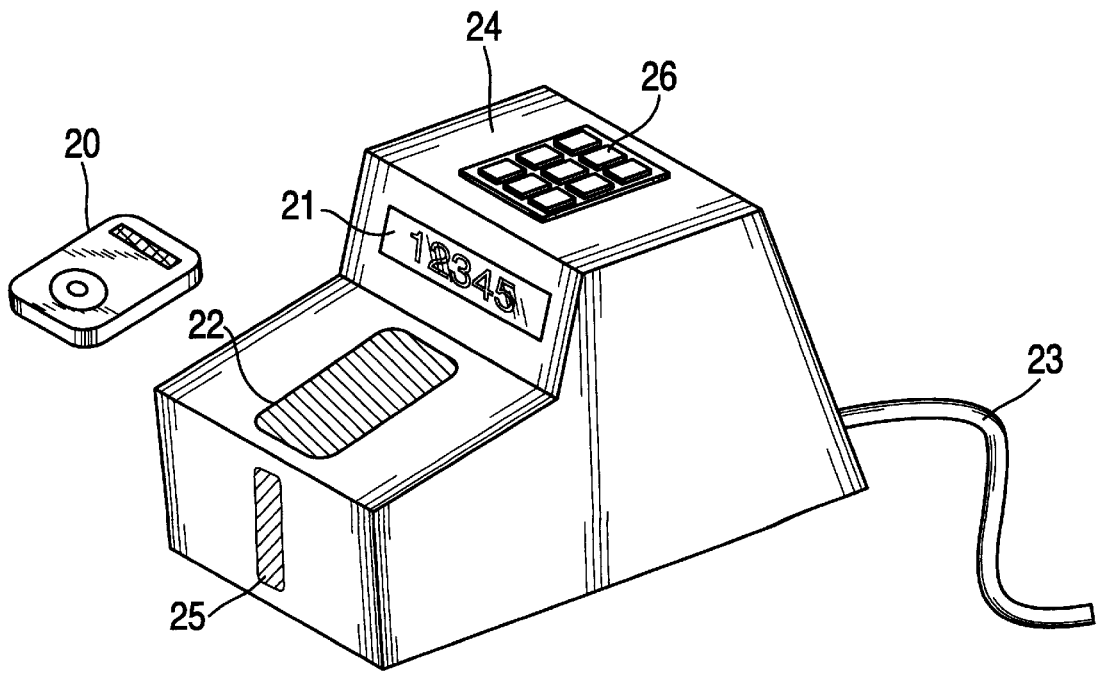
FIG. 4 is an illustration of the console and control keypad.

The operation is illustrated in FIG. 4. The disposable analysis device (20) is used in the manner described above to analyze a sample of fluids. When finished, the result of the analysis is displayed on the screen of the disposable device. At this time, the device is brought into the vicinity of a reader or console, shown diagrammatically as (24). A visual indicator (22) shows the best place for location and an indentation in the console allows the disposable device to be placed and remain there, but in practice anywhere within a few centimeter range will work.

The operator can enter the sample identification information, and other pertinent data such as the operator identification and security code, via a keyboard (26) or other suitable data entry device included in the console.

The reader sends interrogation signals to the disposable device via a coil (not shown) under the orientation pad (22). These signals are detected by the disposable device, which then responds by modulating the signal to or electrical characteristics of the internal coil (17) with a code, which modulation can be read by the console. The modulation is designed to be of low power consumption, and preferably represents a coded digital signal. The modulation could be active or passive. Active modulation of a coil for low power telemetry is well known to a person skilled in the art and is used in many implantable medical devices such as pacemakers.

Several passive techniques will be also readily apparent to one skilled in the art, including switching on and switching off turns of the coil (thus modifying the inductance and resonant frequency which can be remotely detected); connecting and disconnecting a capacitor which modulates the resonant frequency and Q (quality factor); or open circuiting or short circuiting the coil (which modulates the reflected energy and phase thereof). Examples of passive telemetry systems abound, from in store anti-theft devices to cattle identification tags.

Information sent from the disposable device to the console includes the results of the test, plus administrative information which is encoded into the on-chip memory at the time of manufacture, such as type of test(s), calibration information, and date of manufacture. Some of this administrative information could also be included in a bar code printed on the label of the disposable device which is read by a bar code reader shown diagramatically as (25) in the console.

When the communication is complete, a display screen on the console (21) shows the same number as the display screen on the disposable device, and other information depending on the application, to indicate to the user that the information communication has been successful. A microprocessor and associated electronics in the console stores several readings. The console is connected with the hospital or laboratory information system via an electrical connection shown as a cable (23), which could be serial line, universal serial bus, ethernet or any of a variety of suitable hardware and software protocols.

The communications scheme as described above works perfectly well when the communication is done within a short time of the results becoming available, and when power can still be drawn from the internal electrochemical cell. However, there are circumstances where it will not be possible to communicate the results to the reader before the power from the cell is exhausted, for example, a device for water pollution monitoring where the sample is tested at a remote site.

A variation of the above described invention will cope with these circumstances. In this embodiment, the microprocessor system contains a memory device which retains its content when power is removed. There are many types of memory devices with this desirable characteristic, as will be apparent to one skilled in the art. Once the results of the analysis have been determined and displayed on the LCD display, the microprocessor also writes the results to its built in memory so that when power is no longer available, the data are still retained.

When the device is brought in proximity to the console as shown in FIG. 4, the electronics in the console can determine the presence of the disposable device because the interrogation signal sent out from the coil is reflected back from the coil in the disposable device. At this time, the console increases the power supplied to the coil in bursts of energy (typically in the range 10 kHz to 1 MHz), providing information as well as power by inductive coupling to the disposable device, and this power is converted to direct current by circuitry in the disposable device. A scheme for transmitting both power and information over a comparable range has been described in an earlier invention by the present inventor and others, Cochlear Implant System for an Auditory Prosthesis, U.S. Pat. No. 4,532,930.

The disposable device itself then communicates the information back to the reader by means of the same or a different coil. There are many suitable telemetry schemes available, for example, the systems used in implantable pacemakers and defibrillators for communicating information.

In an alternative embodiment of a diagnostic device, the device does not contain a battery for providing power to the device, but instead contains a large value capacitor. The diagnostic device is brought in proximity to a console which senses the presence of the diagnostic device, and then transmits power to the diagnostic device by inductive coupling as described above to activate the device. Circuitry in the diagnostic device charges the capacitor which stores sufficient power to operate the electronics for an adequate time to perform the diagnostic test, and store the results in the on board memory, which is then read by the console as described above.

There are several alternatives to inductive telemetry for communication of information between the disposable device and the reader, including optoelectronic, acoustic, radio frequency transmission, and the like. Any or all of these possibilities could work provided power is available.

The preferred embodiment of this invention has been described in relation to a disposable device for performing chemical or biological assays on a sample of body fluid. Clearly, the invention is also applicable to non-biological applications which have the presence of a fluid, such as pollution monitoring, industrial process monitoring, or detection of biological warfare agents. In these cases, the test performed may not necessarily include a biochemical assay, but could be passive tests such as optical determination of turbidity or cloudiness of a sample, or electrical conductivity of water to determine salinity or acidity (pH). In these cases, the physical arrangement of the assay device is likely to be different, but the method of using a portion of the introduced fluid to provide both power and timing signals, and non-contact telemetry of results, are applicable.

There are some applications where timing information is irrelevant, because there is not the need to wait until a chemical reaction has occurred before the results can be read. An example of this application is a measure of the electrical conductivity of the fluid sample, such as desalinated water. In these applications, there is no need to have a separate cell to provide timing information, and therefore only one cell is provided, which is nevertheless activated by introduction of the fluid sample, immediately powering the device.

Although the present invention has been described with reference to several particular embodiments, it is to be understood that these embodiments are merely illustrative of the application of the principles of the invention. Accordingly, the embodiments described in particular should be considered exemplary, not limiting, with respect to the following claims.

What I claim is:

1. A fluid testing device comprising an analytical system for performing a test on an introduced fluid sample to determine a characteristic of said introduced fluid, an output circuit for providing information indicative of said characteristic, and an electrochemical battery for powering at least one of said analytical system and said output circuit, whose electrolyte includes at least in part the introduced fluid sample.

2. A fluid testing device in accordance with claim 1 wherein the only electrolyte for said electrochemical battery is the introduced fluid sample.

3. A fluid testing device in accordance with claim 1 wherein said electrochemical battery includes two cells which are operated in sequence.

4. A fluid testing device in accordance with claim 3 further including a porous membrane for carrying the introduced fluid sample from one end to the other, with said two cells being positioned along said membrane so that they are operated in sequence.

5. A fluid testing device in accordance with claim 4 further including a microprocessor in said output circuit, the first cell that is configured to power said microprocessor, and the second cell that is configured to turn on the microprocessor following which it is powered by said first cell.

6. A fluid testing device in accordance with claim 5 wherein by the time said second cell is operated said analytic test has been completed.

7. A fluid testing device in accordance with claim 1 wherein said output circuit determines the results of the analytic test and represents them on a self-contained display.

8. A fluid testing device in accordance with claim 1 wherein said output circuit communicates with a console.

9. A fluid testing device in accordance with claim 8 wherein said device is insertable into and contacts said console.

10. A fluid testing device in accordance with claim 8 wherein said device communicates with said console by telemetry without making direct electrical contact therewith.

11. A fluid testing device in accordance with claim 10 wherein the device responds to an interrogation signal transmitted from said console.

12. A fluid testing device in accordance with claim 11 wherein at least one of the said analytical system and said output circuit is powered by the interrogation signal transmitted from said console.

13. A fluid testing device in accordance with claim 1 further including a memory for storing the results of said test.

14. A fluid testing device in accordance with claim 1 where the fluid is a body fluid.

15. A fluid testing device in accordance with claim 1 where the analytic test is an in vitro diagnostic test.

16. A fluid testing device in accordance with claim 1 where the analytic test is pollution monitoring.

17. An electrochemical battery comprising at least two cells, each of which consists of electrodes, a porous separator membrane, and an electrolyte, the porous separator membrane separating the two cells, wherein the electrolyte includes at least in part an introduced fluid, and, wherein said two cells are positioned along said membrane to a time delay by the diffusion of said electrolyte along said membrane between the activation of said first cell and the activation of said second cell.

18. An electrochemical battery in accordance with claim 17 wherein the only electrolyte for said electrochemical battery is the introduced fluid.

19. An electrochemical battery in accordance with claim 17 wherein at leas t one o f said porous membrane or said electrodes carries a dry salt that is dissolved upon introduction of said fluid to form at least part of said electrolyte.

20. An electrochemical battery in accordance with claim 17 further including a connected microprocessor, the first cell being configured to power said microprocessor, and the second cell being configured to activate the microprocessor following which it is powered by said first cell.

21. An electrochemical battery in accordance with claim 20 wherein the activation of said second cell is delayed to allow the production of power by said first cell before the activation of said microprocessor.

22. An electrochemical battery in accordance with claim 17 wherein the two cells have one electrode in common.

23. An electrochemical battery in accordance with claim 17 wherein at least one of the said electrodes is a flexible printed circuit board conductor.

24. An electrochemical battery in accordance with claim 17 wherein at least one of said electrodes is a wire.

25. An electrochemical battery in accordance with claim 17 wherein the electrodes and separator membrane are folded or rolled to conserve space.

26. A method for performing one or more analytic tests on a fluid sample, comprising the steps of:
introducing the fluid sample to an assay device;
using a sensor to analyze said fluid sample to determine a characteristic associated with said fluid sample;
using at least a part of said fluid sample in said device for providing at least part of the electrolyte of an electrochemical battery, said battery being configured to provide power to said sensor.

27. A method in accordance with claim 26 which further includes the method of communicating the results of one or more tests to a console using an output circuit.

28. A method in accordance with claim 27 where said console communicates with said assay device via telemetry.

29. A method in accordance with claim 27 wherein said console communicates with said device optically.

30. A method in accordance with claim 26 wherein said output circuit is powered by a signal transmitted from said console.

31. A method in accordance with claim 26 wherein said electrochemical battery includes two cells, and a porous membrane for carrying the introduced fluid sample from one end to the other, with said two cells being positioned along said membrane so that they are operated in sequence, and operating a microprocessor in the performance of said one or more tests, the first cell that is configured to power said microprocessor, and the second cell that is configured to turn on the microprocessor following which it is powered by said first cell.

32. A method in accordance with claim 31 wherein by the time said second cell is operated said one or more tests have been completed and the results are available.

* * * * *